United States Patent
Afanasewicz et al.

(10) Patent No.: US 8,805,470 B2
(45) Date of Patent: Aug. 12, 2014

(54) DEVICE WITH ENCAPSULATED GEL

(75) Inventors: Elizabeth A. Afanasewicz, Chestnut Hill, MA (US); Robert P. Harhen, Haverhill, MA (US); Adam J. Young, Dedham, MA (US); Rafael M. Cordero, Bedford, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/546,126

(22) Filed: Jul. 11, 2012

(65) Prior Publication Data

US 2013/0023748 A1    Jan. 24, 2013

Related U.S. Application Data

(60) Provisional application No. 61/506,357, filed on Jul. 11, 2011.

(51) Int. Cl.
*A61B 5/04* (2006.01)
*A61N 1/04* (2006.01)

(52) U.S. Cl.
USPC ............ 600/397; 600/391; 600/392; 607/153

(58) Field of Classification Search
CPC ................. A61B 5/04025; A61B 5/04026
USPC ............. 600/391, 392, 397; 607/153
See application file for complete search history.

(56) References Cited

U.S. PATENT DOCUMENTS

| | | | | |
|---|---|---|---|---|
| 3,306,292 A * | 2/1967 | Spees | .......................... | 604/306 |
| 3,340,868 A * | 9/1967 | Darling | .......................... | 600/392 |
| 3,580,254 A * | 5/1971 | Stuart | ............................ | 604/290 |
| 3,636,922 A * | 1/1972 | Ketner | ............................ | 118/264 |
| 3,702,613 A * | 11/1972 | Panico et al. | ................. | 607/142 |
| 4,079,731 A * | 3/1978 | Danby | .......................... | 600/392 |
| 4,526,176 A * | 7/1985 | Bremer et al. | ................ | 600/392 |
| 4,559,950 A * | 12/1985 | Vaughan et al. | ............. | 600/394 |
| 5,135,262 A | 8/1992 | Smith et al. | | |
| 5,305,746 A | 4/1994 | Fendrock | | |
| 5,309,909 A * | 5/1994 | Gadsby et al. | ................ | 600/386 |
| 6,723,077 B2 | 4/2004 | Pickup et al. | | |
| 7,047,054 B2 | 5/2006 | Benni | | |
| 7,269,462 B2 * | 9/2007 | White et al. | .................. | 607/153 |
| 7,865,236 B2 * | 1/2011 | Cory et al. | ..................... | 600/547 |
| 8,275,441 B2 * | 9/2012 | Copp et al. | .................... | 600/396 |
| 8,280,481 B2 * | 10/2012 | Copp et al. | .................... | 600/396 |
| 8,346,375 B2 * | 1/2013 | Jonsen et al. | ................. | 607/142 |
| 2004/0087916 A1 | 5/2004 | Pickup et al. | | |
| 2004/0181196 A1 | 9/2004 | Pickup et al. | | |
| 2006/0020179 A1 | 1/2006 | Anderson et al. | | |
| 2007/0100218 A1 | 5/2007 | Sweitzer et al. | | |
| 2007/0100219 A1 | 5/2007 | Sweitzer et al. | | |
| 2007/0249981 A1 | 10/2007 | Hurwitz et al. | | |
| 2008/0091089 A1 | 4/2008 | Guillory et al. | | |
| 2008/0091090 A1 | 4/2008 | Guillory et al. | | |
| 2013/0023749 A1 | 1/2013 | Afanasewicz et al. | | |

\* cited by examiner

*Primary Examiner* — Lee S Cohen
(74) *Attorney, Agent, or Firm* — Shvarts & Leiz LLP

(57) ABSTRACT

Apparatus and techniques are provided for interfacing a device with a surface. The apparatus and techniques provide gel encapsulation and isolation mechanisms to extend the shelf-life of the preparation devices, allow for the use of more effective materials, and improve the quality of the contact between a device and an application surface. Particular embodiments of these apparatus and techniques suitable for use in medical contexts are also provided.

24 Claims, 5 Drawing Sheets

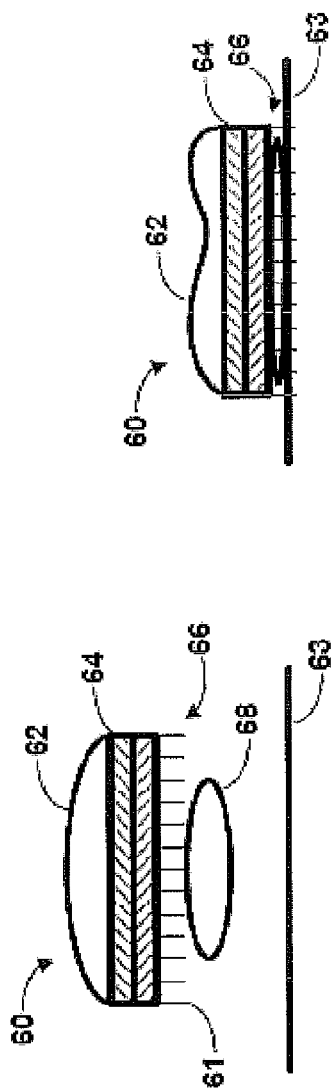
FIG. 6A
FIG. 6B
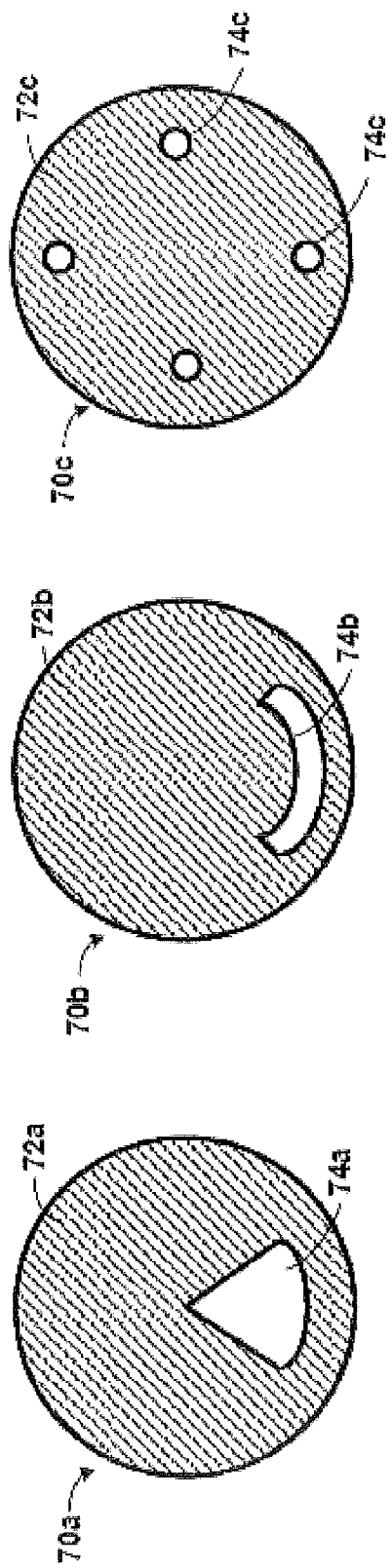
FIG. 7A
FIG. 7B
FIG. 7C

DEVICE WITH ENCAPSULATED GEL

SUMMARY OF THE DISCLOSURE

Many procedures involve the preparation of a surface before interfacing the surface with a device. For example, in medical contexts, a monitoring or treatment device, such as a self-prepping electrode including tines or microneedles, may be pressed toward the skin to create microconduits for conductive gel in the upper layers of a patient's skin. Such self-prepping electrodes are often "pre-gelled," meaning that the conductive gel is disposed on the surface of an electrode during packaging so that an operator may simply open the package and apply the electrode to a patient. However, some liquids and gels designed to couple a device to a surface may degrade the performance of the device when packaged in contact with the device. For example, liquid conductive gels in contact with a surface electrode (such as a Ag or Ag/AgCl electrode) will corrode the electrode surface, hampering performance. While conductive gels with high salt content improve the interface between a subject surface (e.g., a patient's tissue) and an electrode, higher salt contents may lead to faster corrosion and limit the shelf-life of the preparation device.

Described herein are apparatus and techniques for a preparation device that address the challenges described above. These apparatus and techniques provide gel encapsulation and isolation mechanisms to extend the shelf-life of the preparation devices, allow for the use of more effective materials, and improve the quality of the contact between a device and an application surface. Particular embodiments of these apparatus and techniques suitable for use in medical contexts are also provided.

BRIEF DESCRIPTION OF THE DRAWINGS

FIGS. 6A-6B depict the operation of an illustrative preparation device in accordance with an embodiment;

FIGS. 7A-7C are top views of illustrative preparation devices with windows in accordance with various embodiments;

DETAILED DESCRIPTION

Figure 1:
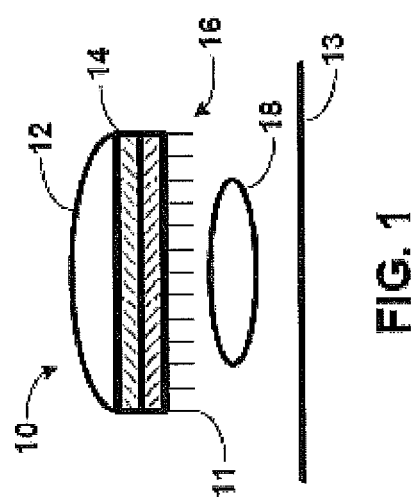
FIG. 1 is a partially exploded side view of an illustrative preparation device in accordance with an embodiment.

FIG. 1 is a partially exploded side view of an illustrative preparation device 10 in accordance with an embodiment. As illustrated, preparation device 10 includes actuation surface 12, intermediate portion 14, and contact portion 16 (which includes tines 11). Preparation device 10 may also include capsule 18. Capsule 18 may be a homogeneous material, such as a gel droplet, a collection of materials (such as a porous material soaked with a liquid), or may include a membrane surrounding a liquid, a gel, a powder, a vapor, or any other suitable material. In an embodiment, when capsule 18 is positioned between actuation surface 12 and subject surface 13, applying a downward force (i.e., towards subject surface 13) to actuation surface 12 may cause contact portion 16 to compress capsule 18 and release its contents.

There are many mechanisms by which capsule 18 may release its contents when a suitable pressure is applied to actuation surface 12. In certain embodiments, applying a downward force to actuation surface 12 causes contact portion 16 to burst capsule 18. In certain embodiments, applying a downward force to actuation surface 12 causes contact portion 16 to pierce capsule 18 (e.g., with tines 11 or an additional piercing member, not shown). Capsule 18 may be pierced by one or more of tines 11. Capsule 18 may be configured to deform or release its contents only when a suitable compression force has been applied.

When a surface is to be prepared, the desired force or force thresholds may vary. For example, when the surface to be prepared is the tissue of an animal subject, the desired force of preparation may depend at least in part on a medical protocol to be implemented after the preparation.

As illustrated, preparation device 10 may also include intermediate portion 14. In medical applications, intermediate portion 14 may be a sensing device (such as a passive electrode) or a treatment device (such as an active electrode), as discussed in additional detail below. In the embodiment of FIG. 1, intermediate portion 14 is positioned between actuation surface 12 and contact portion 16. In alternate embodiments, intermediate portion 14 may be positioned between contact portion 16 and preparation surface 13. In such embodiments, contact portion 16 may be capable of penetrating intermediate portion 14 to contact preparation surface 13. Such a mechanism may be enabled in any of a number of ways. For example, intermediate portion 14 may be a porous material, such as a sponge (which may be made from or embedded with conductive filaments if electrical conductivity is desired). In an embodiment, intermediate portion 14 may be a woven or perforated screen, which may be a conductive screen. As is also illustrated in the embodiments described herein, contact portions and intermediate portions may be configured in any of a number of orientations relative to the surface which is to be prepared (e.g., adjacent, vertically oriented, opposed, etc.).

Figure 2:
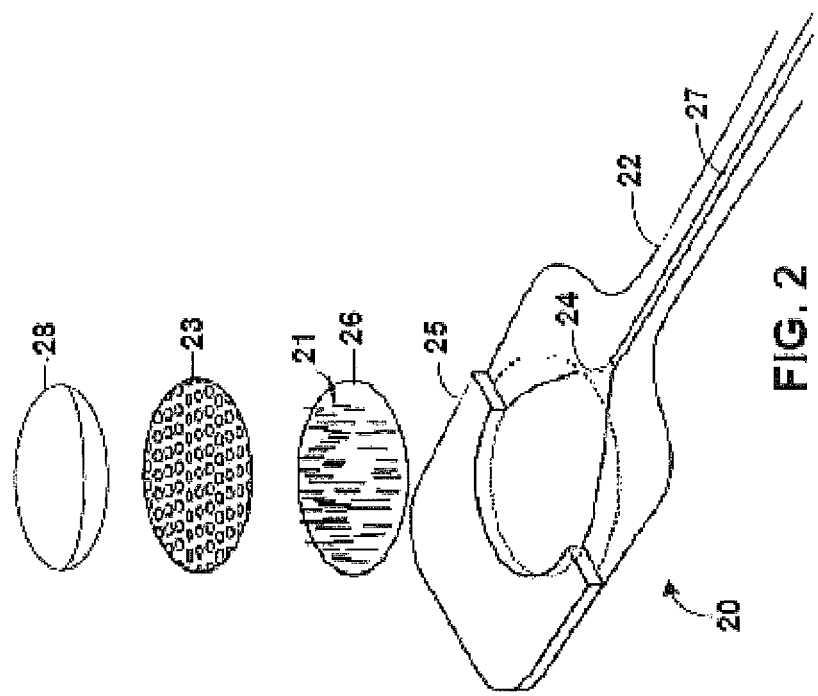
FIG. 2 is an exploded perspective view of an illustrative preparation device in accordance with an embodiment.

To illustrate a use of the preparation techniques described herein, an exemplary embodiments of a medical device incorporating a preparation device will now be described. FIG. 2 is an exploded perspective view of electrode structure 20. In the embodiment of FIG. 2, a flexible circuit may be created by printing a layer of conductive Ag/AgCl ink 24 on flexible substrate 22 (formed from a material such as Mylar or polyester). Other embodiments may utilize carbon, nickel, copper and/or other metal inks.

Basepad 25 (shown with a portion cut away) of 1/16" double-sided adhesive foam with a circular hole of 0.6" diameter, may be placed onto substrate 22 so that the hole is centered concentric to the eyelet. In an embodiment, basepad 25 may include a polyethylene foam. A hole in basepad 25 creates a cylindrical housing which may be used to contain a liquid gel once the gel is released from ellipsoidal capsule 28, as discussed further below. It will be understood that a hole in basepad 25 may be any suitable shape, such as an ellipse, a polygon, or a shape in conformance with a capsule (such as capsule 28), a body region, an electrode area, or the contact surface of any other device.

Electrode 20 may additionally include studded, porous spacer disc 26, which may be approximately 0.6 inches in diameter and made from Velcro hook material. Hooks 21 on disc 26 may be sheared to make tines that may serve as a skin prepping mechanism when a force is applied to disc 26. These tines may prepare the skin as described in U.S. Pat. No. 5,305,746 issued to Fendrock and incorporated by reference in its entirety herein. The backing of disc 26 may be porous to allow a gel or other conductive fluid to go through it, which may consequently provide full conductivity in the direction perpendicular to the electrode substrate. In an embodiment, the Velcro thickness including the tine profile may be approximately 0.08 inches. After release from capsule 28, liquid gel may be held in the cylindrical housing by porous spacer sponge 23, which may be made out of a porous material (e.g., a urethane open pore sponge).

Flexible printed trace 27 may electrically connect the electrode to a cable connector (not shown) or to another electrical device. A cable connector may allow the electrode to be connected to a data acquisition system or to a medical therapy delivery unit.

Figure 3B:
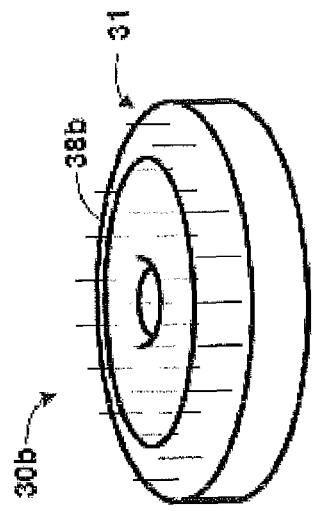
FIGS. 3A-3D depict a portion of illustrative preparation devices in accordance with various embodiments.
Figure 3D:
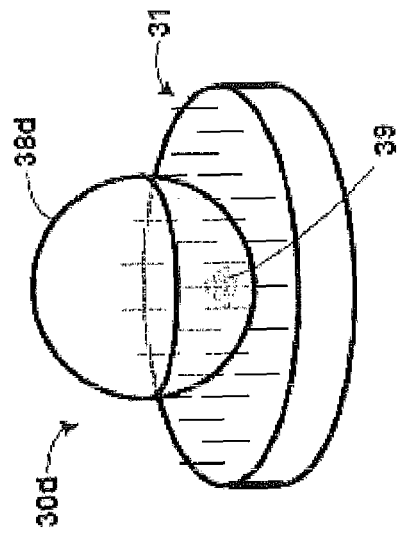
Figure 3A:
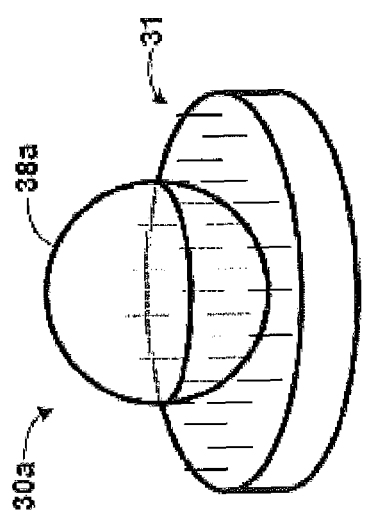

FIGS. 3A-3D depict illustrative preparation devices in accordance with various embodiments. In particular, FIGS. 3A-3D depict an underside view of several embodiments of preparation devices. In certain embodiments, a capsule may be in contact with at least one of a plurality of tines included in a contact portion prior to compressing the capsule. For example, preparation device 30a of FIG. 3A depicts spherical capsule 38a positioned above tines 31. Preparation device 30b of FIG. 3B depicts toroidal capsule 38b positioned above tines 31.

Figure 3C:
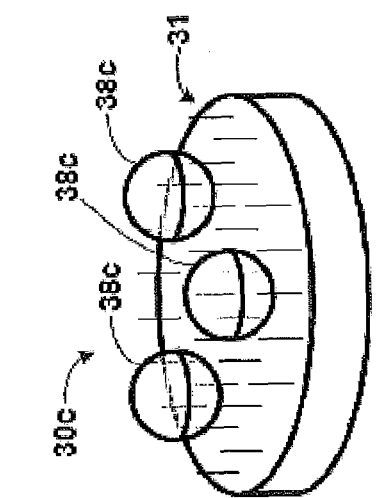

Preparation device 30c of FIG. 3C depicts a plurality of capsules 38c positioned above tines 31. The plurality of capsules 38c may include identical capsules, or capsules of differing size, content or composition. Although three capsules 38c are illustrated in FIG. 3C, any suitable number of capsules may be used. In an embodiment, capsules small enough to fit into the inter-tine spaces of a contact surface may be used.

Preparation device 30d of FIG. 3D depicts capsule 38d positioned above tines 31 and above piercing member 39. Piercing member 39 may be a specially-configured and/or positioned member capable of releasing the contents of capsule 38d when a sufficient contact pressure is exerted between them. Piercing member 39 may take any suitable shape, such as a pyramid, obelisk, or spike. Piercing member 39 may be formed substantially similarly to any of tines 31, and may include additional support or strengthening members to improve its ability to pierce capsule 38d.

Figure 4A:
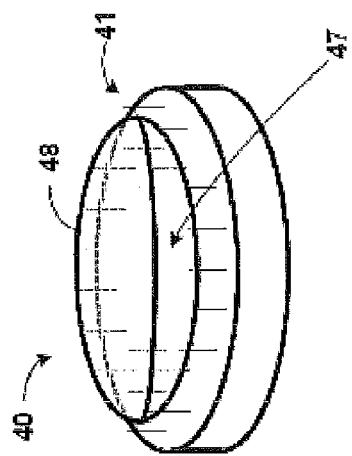
FIGS. 4A-4B depict a portion of an illustrative preparation device in accordance with an embodiment.
Figure 4B:
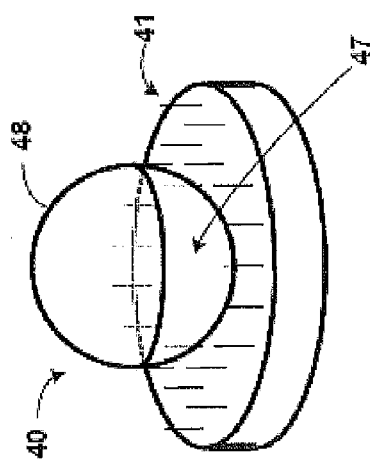

FIGS. 4A-4B depict a portion of illustrative preparation device 40 in accordance with an embodiment. FIG. 4A depicts a configuration in which capsule 48 is positioned above tine-free region 47, and is thus not in contact with any of the plurality of tines 41 prior to compressing capsule 48. When capsule 48 is compressed as illustrated in FIG. 4B (e.g., as described above with reference to FIG. 1 and discussed in additional detail below), capsule 48 is deformed and brought into contact with at least one of the plurality of tines 31. At least one of the plurality of tines 31 may pierce capsule 48 in the deformed state of FIG. 4B, which may cause capsule 48 to release its contents.

Various embodiments of the devices disclosed herein may include capsules configured for selective deformation and/or release of contents when compressed. For example, a capsule may include a number of different sections or volumes of different materials arranged so that, when the capsule is compressed, the different materials will contact a preparation surface in a predetermined pattern (which may, for example, encourage mixing of the different materials, or apply different materials to different areas of the surface to achieve a desired preparation effect).

Figure 5A:
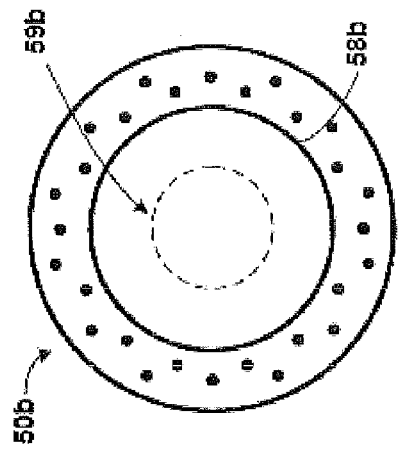
FIGS. 5A-5B are bottom views of illustrative preparation devices including capsules with membrane regions in accordance with various embodiments.
Figure 5B:
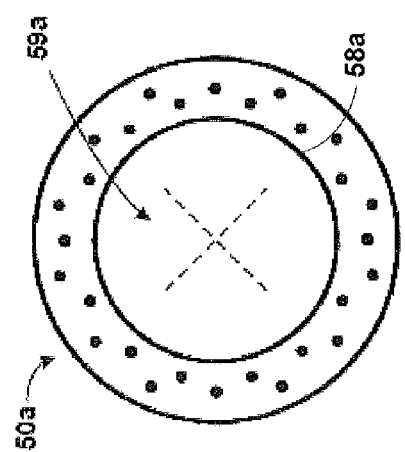

In certain embodiments, mechanical properties of a capsule may be configured to control the capsule's deformation under compression. For example, a portion of a membrane of a capsule may be selectively treated to encourage that membrane portion to rupture when the capsule is compressed. FIGS. 5A-5B are bottom views of illustrative preparation devices including capsules with membrane regions in accordance with certain embodiments. Preparation device 50a of FIG. 5A depicts capsule 58a with an 'X' figure scored into its surface in membrane region 59a. Preparation device 50b of FIG. 5B depicts capsule 58b with a thinned membrane region 59b (indicated by the dashed circle).

FIGS. 6A-6B depict the operation of illustrative preparation device 60 in accordance with an embodiment. As described above with reference to FIG. 1, FIG. 6A depicts a partially exploded side view of an illustrative preparation device 60, including actuation surface 62, intermediate portion 64, contact portion 66 (which includes tines 61), and capsule 68. In an embodiment, actuation surface 62 may have a profile adapted to guide an operator in applying a downward force at the correct location, such as a concave profile, a combination concave/convex profile, or a protruding profile as illustrated. When capsule 68 is positioned between actuation surface 62 and subject surface 63, applying a downward force (i.e., towards subject surface 63) to actuation surface 62 may cause contact portion 66 to compress capsule 68, as depicted in FIG. 6B. Additionally, applying a downward force to actuation surface 62 may cause actuation surface 62 to change shape (e.g., deform or collapse). This shape change may provide a visual and/or tactile feedback mechanism to an operator, indicating that preparation device 60 has been actuated. A shape change may be permanent (which may be advantageous for "single-use" preparation devices) or may be reversible (for preparation devices capable of repeated use).

As previously mentioned, certain of the apparatus and techniques described herein for surface preparation may provide a feedback mechanism to an operator. A feedback mechanism may alert an operator when a preparation device has been actuated and/or when a surface is appropriately prepared. In an embodiment, tactile feedback provided to an operator of a preparation device may arise from the breaking or crushing of an element embedded in the preparation device. For example, as described above, a preparation device may include a capsule, such as a sealed capsule containing air, gel, or another fluid. This capsule may be positioned between an actuation surface of a skin preparation device and the surface which is to be prepared, or in any appropriate location. When a suitable force is applied to the capsule during operation of the preparation device, the capsule may yield to the force and deform or break. An operator of the preparation device may be able to detect this occurrence tactilely, which may indicate that a sufficient pressure has been applied.

In an embodiment, a feedback mechanism may provide another type of visual feedback to an operator, such as one or more of a color change and a shape change. A color change may occur by any of a number of mechanical, chemical and/or electrical mechanisms. In an embodiment, a preparation device may include a material or chemical composition that changes color under stress or deformation. Such materials are often used in tamper-evident packaging and labeling. Such materials are often used in tamper-evident packaging and labeling. Examples of such materials are provided by Smith et al., U.S. Pat. No. 5,135,262, entitled "METHOD OF MAKING COLOR CHANGE DEVICES ACTIVATABLE BY BENDING AND PRODUCT THEREOF," which is incorporated by reference in its entirety herein.

In an embodiment, a chemical reaction may produce a color change that provides feedback to an operator. Such a chemical reaction may involve the interaction between a previously-contained substance (such as a liquid or gel) and air, or between the previously-contained substance and another substance (e.g., as occurs in the luminescent reaction underlying glow stick operation), once the container for the previously-contained substance has been broken or opened. A color change may occur when a colored substance previously hidden falls within an operator's view; for example, a colored gel contained in a capsule which deforms and/or releases its contents under compression and which can subsequently be seen by an operator. A color change may also occur when a substance has been exposed to air for a threshold period of time, indicating that the preparation device should be discarded or replaced.

An operator may be able to view a color change or other capsule compression-related event through one or more windows in a preparation device. Such windows may be located in a top surface of a preparation device (e.g., in or near an actuation surface), or in any other surface of the preparation capable of being seen by an operator. A window may be an unfilled aperture, an aperture filled with or covered by a transparent or translucent material, or a transparent or translucent portion of a top surface of a preparation device. FIGS. 7A-7C are top views of illustrative preparation devices with windows in accordance with various embodiments. Preparation device 70a of FIG. 7A includes a top surface 72a (which may be an actuation surface) with wedge-shaped window 74a. Preparation device 70b of FIG. 7B includes a top surface 72b (which may be an actuation surface) with elongated window 74b. Elongated window 74b is depicted as located along the periphery of top surface 72b, which may allow an operator to determine when an underlying capsule or the contents of such a capsule has spread to the periphery of the preparation device. Preparation device 70c of FIG. 7C includes a top surface 72c (which may be an actuation surface) with a plurality of windows 74c. Although four windows 74c are illustrated in FIG. 7C, any suitable number and arrangement of windows may be used.

In an embodiment, a feedback mechanism may include an electronic indicator. For example, a preparation device may include an LED. Upon actuating a skin preparation device as described herein, LED 81 may light up as an indicator to an operator. A lit LED may indicate any one or more of a number of conditions to an operator, including when a physical event has occurred (e.g., when a lubricating or conducting gel capsule has burst), when an electrical condition has occurred (e.g., when a compressed capsule has enabled a desired electrical connection, for example, between the surface and the preparation device and/or two regions of the preparation device), when contact between the preparation device and the surface has been maintained for a sufficient amount of time for successful preparation, and when contact between the preparation device and the surface has been maintained for a maximum allowable amount of time (i.e., the preparation device should be checked, removed or replaced). An electronic indicator may be controlled by a processing device located within the device, within the device applicator, or within a system in electronic communication with the device or device applicator (such as a monitoring or treatment system). In any of the embodiments described herein, electronic communication may occur through wired or wireless transmission.

Figure 8A:
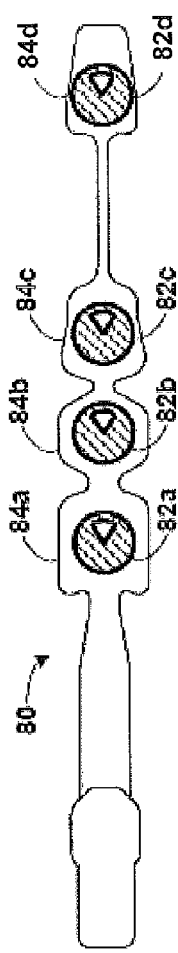
FIGS. 8A-8B are top and bottom views, respectively, of a illustrative medical device configured to be used with the preparation devices and techniques described herein.
Figure 8B:
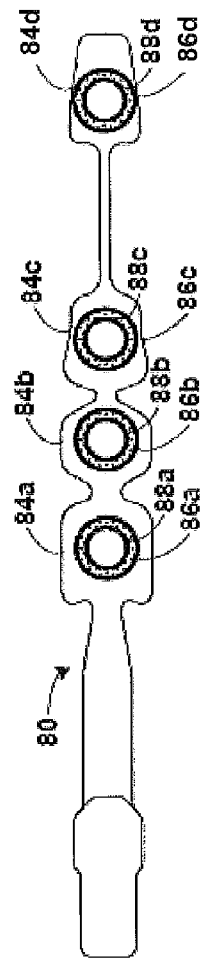

The device application apparatus and techniques described herein may be used with devices that contain one or more than one contact portion or regions that should come in contact with a surface. For example, FIGS. 8A and 8B depict top and bottom views, respectively, of a illustrative medical device 80 configured to be applied in accordance with the preparation techniques described herein. Medical device 80 may include regions 84a, 84b, 84c and 84d, each of which includes a contact portion 86a, 86b, 86c and 86d, respectively, that is adapted to contact a subject's tissue (e.g., skin). In FIG. 8A, actuation surfaces 82a, 82b, 82c and 82d are illustrated as integrated with the medical device in regions 84a, 84b, 84c and 84d, respectively. In the embodiment of FIG. 8B, capsules 88a, 88b, 88c and 88d may be included in regions 84a, 84b, 84c and 84d, respectively. A capsule may be a closed or porous material (e.g., a sponge) containing a gel or other fluid that may be usefully applied at the interface between the subject's tissue and the contact portions. For example, when a medical device includes an electrode or array of electrodes (active or passive), a capsule may contain a conductive gel to improve the coupling between the subject's tissue and the electrodes. A capsule may include an adhesive membrane and/or contain an adhesive fluid to improve adhesion between the subject's tissue and the device. As discussed above, a capsule may burst when the device is applied to the subject's tissue, providing tactile feedback to an operator.

Figure 8C:
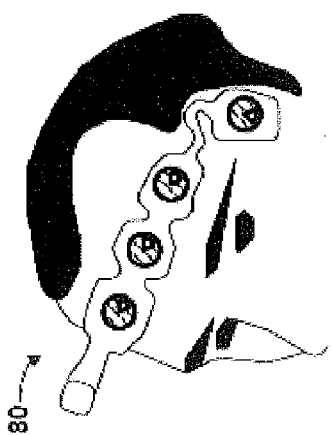
FIG. 8C depicts the illustrative medical device of FIGS. 8A-8B as applied to a subject's forehead in accordance with an embodiment.

FIG. 8C depicts medical device 80 of FIGS. 8A and 8B as applied to a subject's forehead in accordance with an embodiment. When a flexible underlying substrate is used to integrate regions 84a, 84b, 84c and 84d into device 80, device 80 may be adjustably positioned to conform to a subject's anatomy for successful monitoring and/or treatment. The preparation devices of regions 84a, 84b, 84c and 84d may not be identically constructed. In an embodiment, preparation devices may differ in any of the ways described herein. The properties of the preparation device used for a specific application or surface region may depend on a number of factors, including monitoring characteristics, treatment characteristics, subject/surface characteristics and environmental conditions.

Figure 9:
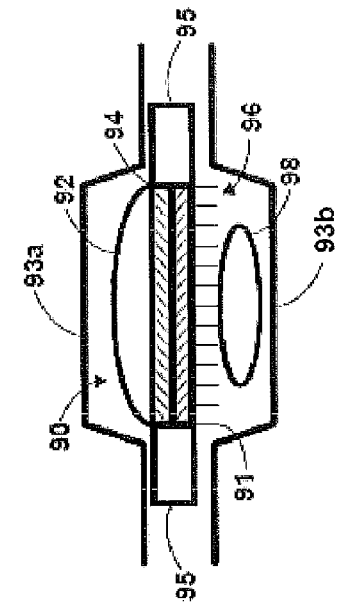
FIG. 9 is a side view of a preparation device in illustrative packaging, in accordance with an embodiment.

FIG. 9 is a side view of preparation device 90 in illustrative packaging, in accordance with an embodiment. As discussed above, preparation device 90 may include actuation surface 92, intermediate portion 94, contact portion 96, capsule 98 and tines 91. Preparation device 90 may also include tabs 95, which may be constructed in the manner described above with reference to basepad 25 of FIG. 2. Tabs 95 may or may not include an adhesive on their surface-contacting face. The packaging of preparation device 90 may include upper housing 93a and lower housing 93b. Housings 93a and 93b may be composed of any suitable material, including any suitable plastic, and may be disposable or reusable. In an embodiment, the contact between tabs 95 and lower housing 93b seals capsule 98, preventing drying out of capsule 98. In an embodiment, capsule 98 is not sealed between tabs 95 and lower housing 93b. As discussed above, encapsulating a gel within a membrane may allow capsule 98 to be exposed to air without drying out, thus simplifying the manufacturing and packaging process and extending shelf life.

One advantage of the preparation devices and techniques described herein is the isolation between a capsule and/or its contents and other components of the preparation device (e.g., an intermediate portion including an electrode) which may be sensitive to the capsule and/or its contents. For example, liquid conductive gels in contact with a surface electrode (such as a Ag or Ag/AgCl electrode) will corrode the electrode surface, hampering performance. While conductive gels with high salt content improve the interface between a subject surface (e.g., a patient's tissue) and an electrode, higher salt contents may lead to faster corrosion. For preparation devices in which an electrode is pre-packaged in contact with a conductive gel, corrosion may limit the shelf-life of the preparation device. However, packaging a conductive gel in a capsule may limit the contact between the conductive gel and the sensitive electrode, thus prolonging the shelf-life of the device and allowing a higher salt content gel to be used than in other pre-packaged electrodes. In an embodiment, a capsule is spaced away from a sensitive component of the preparation device (e.g., by being adhesively or otherwise attached to the ends of non-conducting tines extending away from the electrode). In an embodiment, a membrane of a capsule provides a barrier between an encapsulated gel and the contact portion of a preparation device. Such a membrane may be made of a less corrosive material than the encapsulated gel. In an embodiment, a membrane may be made of a conductive material so as not to hinder conductivity when the membrane is burst during preparation.

Another embodiment may utilize solid hydrogels instead of or in addition to liquid hydrogels. While solid hydrogels have lower conductivities than liquid gels, their use may be advantageous in certain applications. For example, solid hydrogels may be advantageous for sensors which incorporate closely-spaced multiple electrode sensors. In such an application, the higher material crosslinking of the solid hydrogel prevents shorting of the electrode elements due to gel migration, which would occur if liquid gels were used. Such an embodiment may allows the use of solid hydrogels with higher salt content than is commonly used while maintaining a suitably long shelf life.

Another advantage of the preparation apparatus and techniques described herein is an ease of handling and positioning by an operator. A sealed capsule containing a fluid may not be adhesive to the touch, thereby allowing an operator to slideably adjust the location of the preparation apparatus on a surface without losing fluid or leaving a sticky trace. Sealing the fluid also has the advantage of cleaner application, with no messy packaging to dispose of or contamination of the encapsulated fluid by an operator or environmental contaminants.

The foregoing is merely illustrative of the principles of this disclosure and various modifications can be made by those skilled in the art without departing from the scope and spirit of the disclosure. The following claims may also describe various aspects of this disclosure.

What is claimed is:

1. A device for preparing a subject, comprising:
   at least one capsule containing a gel;
   a contact portion comprising a plurality of tines, positioned above the gel capsule;
   an actuation surface, positioned above the contact portion; and
   a visual feedback mechanism that indicates that the gel has been released, wherein the visual feedback mechanism comprises a color change of the gel;
   wherein, when the capsule of the preparation device is in contact with a subject, applying a downward force to the actuation surface causes the contact portion to compress the capsule and release the gel contained therein.

2. The device of claim 1, wherein the contact portion is configured to burst the capsule and release the gel contained therein upon application of a downward force to the actuation surface.

3. The device of claim 1, wherein the contact portion is configured to pierce the capsule and release the gel contained therein upon application of a downward force to the actuation surface.

4. The device of claim 3, wherein the capsule is configured to be pierced by at least one of the plurality of tines.

5. The device of claim 3, wherein the capsule is configured to be pierced by a piercing member of the contact portion.

6. The device of claim 1, wherein the capsule is configured not to be in contact with any of the plurality of tines prior to compressing the capsule.

7. The device of claim 6, wherein the capsule is configured to come into contact with at least one of the plurality of tines upon compression of the capsule.

8. The device of claim 1, wherein the capsule is configured to be in contact with at least one of the plurality of tines prior to compressing the capsule.

9. The device of claim 1, wherein the actuation surface is concave.

10. The device of claim 1, wherein the capsule comprises a membrane surrounding the gel contained therein.

11. The device of claim 10, wherein the membrane provides a barrier between the gel and the contact portion.

12. The device of claim 11, wherein the membrane comprises a less corrosive material than the gel.

13. The device of claim 11, wherein the contact portion comprises a sensor surface, and the membrane provides a barrier between the gel and the sensor surface.

14. The device of claim 13, wherein the gel and the sensor surface are configured to come into contact when the gel is released from the capsule.

15. The device of claim 10, wherein a portion of the membrane is scored.

16. The device of claim 10, wherein a portion of the membrane is thinned.

17. The device of claim 10, wherein the membrane is comprised of a conductive material.

18. The device of claim 10, wherein at least one of the membrane and the gel is comprised of an adhesive material.

19. The device of claim 1, wherein the capsule is spherical.

20. The device of claim 1, further comprising a plurality of capsules.

21. The device of claim 1, wherein a portion of the actuation surface is translucent.

22. The device of claim 1, wherein the gel is a conductive gel.

23. The device of claim 22, wherein the gel is a high salt content gel.

24. A device for preparing a subject, comprising:
   at least one toroidal capsule containing a gel;
   a contact portion comprising a plurality of tines, positioned above the gel capsule; and
   an actuation surface, positioned above the contact portion;
   wherein, when the capsule of the preparation device is in contact with a subject, applying a downward force to the actuation surface causes the contact portion to compress the capsule and release the gel contained therein.

* * * * *